United States Patent [19]

Roninson et al.

[11] Patent Number: 5,217,889
[45] Date of Patent: Jun. 8, 1993

[54] METHODS AND APPLICATIONS FOR EFFICIENT GENETIC SUPPRESSOR ELEMENTS

[76] Inventors: Igor B. Roninson, 818 S. Laflin St.; Tatyana Holzmayer, 1451 W. Flournoy St., Apt. 2E, both of Chicago, Ill. 60607; Kyunghee Choi, 1121 Albion St., Apt. 806, Denver, Colo. 80220

[21] Appl. No.: 599,730

[22] Filed: Oct. 19, 1990

[51] Int. Cl.[5] .............. C12N 15/10; C12N 1/00; C12N 5/10

[52] U.S. Cl. .............. 435/172.3; 435/240.1; 435/243

[58] Field of Search ............. 435/172.3, 240.1, 240.2, 435/252.3, 252.33; 536/27

[56] References Cited

U.S. PATENT DOCUMENTS 4,753,873 6/1988 Beltz et al. .............. 435/5

OTHER PUBLICATIONS

Takayama et al., Crit. Rev. Biochem. Mol. Biol., vol. 25, 1990, pp. 155-184, (only pp. 176-177 considered).
Rüther et al., PNAS, vol. 79, 1982, pp. 6852-6855.
Nomura et al., Gene, vol. 18, 1982, pp. 239-246.
Robbins et al., J. Mol. Appl. Genet., vol. 2, 1984, pp. 485-496.
Herskowitz, Nature 329: 219-222 (1987).
Friedman et al., Nature 335: 452-454 (1988).
Baltimore, Nature 335: 395-396 (1988).
Green et al., Cell 58: 215-223 (1989).
Rimsky et al., Nature 341: 453-456 (1989).
Trono et al., Cell 59: 113-120 (1989).
Ransone et al., Proc. Natl. Acad. Sci. USA 87: 3806-3810 (1990).
Whitaker-Dowling et al., Virology 175: 358-364 (1990).
Lee et al., J. Bacteriol. 171: 3002-3007 (1989).
Chejanovsky et al., J. Virol. 64: 1764-1770 (1990).
van der Krol et al., BioTechniques 6: 958-976 (1988).
Ch'ng et al., Proc. Natl. Acad. Sci. USA 86: 10006-10010 (1989).
Daugherty et al., Gene Anal. Techn. 6: 1-16 (1989).
Powell et al., Proc. Natl. Acad. Sci. USA 86: 6949-6952 (1989).
Sarver et al., Science 247: 1222-1225 (1990).
Kerr et al., Eur. J. Biochem. 175: 65-73 (1988).
Bunell et al., Somat. Cell. Mol. Genet. 16; 151-162 (1990).

Primary Examiner—Richard A. Schwartz
Assistant Examiner—James Ketter

[57] ABSTRACT

Methods for isolating and identifying genetic elements that are capable of inhibiting gene function are disclosed, as well as genetic elements isolated or identified according to the method of the invention and host cells modified by genetic modification using genetic suppressor elements according to the invention.

3 Claims, No Drawings

METHODS AND APPLICATIONS FOR EFFICIENT GENETIC SUPPRESSOR ELEMENTS

BACKGROUND OF THE INVENTION

1. Field of the Invention

The invention relates to means for suppressing specific gene function in eukaryotic or prokaryotic cells. More particularly the invention relates to the use of expression of DNA sequences, known as genetic suppressor elements, for the purpose of suppressing specific gene function. The invention provides methods for obtaining such genetic suppressor elements, the genetic suppressor elements themselves, and methods for obtaining living cells which bear a gene suppression phenotype.

2. Summary of the Related Art

Functional inactivation of genes through the expression of specific genetic elements comprising all or a part of the gene to be inactivated is known in the art. At least four mechanisms exist by which expression of such specific genetic elements can result in inactivation of their corresponding gene. These are interference with protein function by polypeptides comprising nonfunctional or partly nonfunctional analogs of the protein to be inhibited or a portion thereof, interference with mRNA translation by complementary anti-sense RNA or DNA, destruction of mRNA by anti-sense RNA coupled with ribozymes, and interference with mRNA by RNA sequences homologous to a portion of the mRNA representing an important regulatory sequence.

Herskowitz, Nature 329: 219-222 (1987), reviews the inactivation of genes by interference at the protein level, which is achieved through the expression of specific genetic elements encoding a polypeptide comprising both intact, functional domains of the wild type protein as well as nonfunctional domains of the same wild type protein. Such peptides are known as dominant negative mutant proteins.

Friedman et al., Nature 335: 452-454 (1988), discloses the use of dominant negative mutants derived from HSV-1 VP16 protein by 3' truncation of the VP16 coding sequence to produce cells resistant to herpes-virus infection. Baltimore, Nature 335: 395-396 (1988), suggests that the method might be applicable as a therapeutic means for treatment of HIV-infected individuals.

Green et al., Cell 58: 215-223 (1989), discloses inhibition of gene expression driven by an HIV LTR, through the use of dominant negative mutants derived from the HIV-1 Tat protein sequence, using chemical peptide synthesis.

Rimsky et al., Nature 341: 453-456 (1989), discloses inhibition of HTLV-1 and HIV-1 gene expression in an artificial plasmid system, using dominant negative mutants derived from the HTLV-1 Rex transactivator protein by oligonucleotide-mediated mutagenesis of the rex gene.

Trono et al., Cell 59: 113-120 (1989), demonstrates inhibition of HIV-1 replication in a cell culture system, using dominant negative mutants derived from the HIV-1 Gag protein by linker insertional and deletional mutagenesis of the gag gene.

Ransone et al., Proc. Natl. Acad. Sci. USA 87: 3806-3810 (1990), discloses suppression of DNA binding by the cellular Fos-Jun protein complex and suppression of Jun-mediated transcriptional transactivation, using dominant negative mutants derived from Fax and Jun proteins by oligonucleotide-directed substitutional or deletional mutagenesis of the fos and jun genes.

Whitaker-Dowling et al., Virology 175: 358-364 (1990), discloses a cold-adapted strain of influenza A virus which interferes with production of wild-type influenza A virus in mixed infections, apparently by a dominant negative mutant protein mechanism.

Lee et al., J. Bacteriol. 171: 3002-3007 (1989), discloses a genetic system for isolation of dominant negative mutations of the beta subunit of $E.$ $coli$ RNA polymerase obtained by hydroxylamine mutagenesis of the rpoB gene.

Chejanovsky et al., J. Virol. 64: 1764-1770 (1990), discloses inhibition of adeno-associated virus (AAV) replication by a dominant negative mutant protein derived from the AAV Rep protein by oligonucleotide-directed substitutional mutagenesis of the rep gene at a position encoding an amino acid known to be critical to Rep protein function.

Suppression of specific gene function by interference at the RNA level, using complementary RNA or DNA sequences, is also known in the art. van der Krol et al., BioTechniques 6: 958-976 (1988), reviews the use of such "antisense" genes or nucleotide sequences in the inhibition of gene function in insect, bird, mammalian, plant, protozoal, amphibian and bacterial cells.

Ch'ng et al., Proc. Natl. Acad. Sci. USA 86: 10006-10010 (1989) discloses that antisense RNA complementary to the 3' coding and non-coding sequences of the creatine kinase gene inhibited in vivo translation of creatine kinase mRNA when expressed from a retrovirus vector, whereas all antisense RNAs complementary to creatine kinase mRNA, but without the last 17 codons or 3' non-coding sequences, were not inhibitory.

Daugherty et al., Gene Anal. Techn. 6: 1-16 (1989) discloses that, for antisense RNA suppression of beta galactosidase ($\beta$-gal) gene function in $E.$ $coli$, best suppression is achieved using plasmids containing a ribosome binding site and expressing short RNA sequences corresponding to the 5' end of the $\beta$-gal gene.

Powell et al., Proc. Natl. Acad. Sci. USA 86: 649-6952 (1989), discloses protection of transgenic plants from tobacco mosaic virus (TMV) when the plants expressed sequences complementary to replicase binding sites, but not when they expressed sequences complementary only to TMV coat protein.

Sarver et al., Science 247: 1222-1225 (1990), discloses the use of antisense RNA-ribozyme conjugates to degrade specific mRNA by complementary RNA binding followed by ribozyme cleavage of the bound mRNA.

Kerr et al., Eur. J. Biochem. 175: 65-73 (1988), reports that even full length antisense RNA is not necessarily sufficient to inhibit gene expression.

Inhibition of gene function can also be accomplished by expressing subregions of RNA which is homologous to, rather than complementary to, important regulatory sequences on the mRNA molecule, and which can likely compete with the mRNA for binding regulatory elements important to expression.

Bunnell et al., Somat. Cell Mol. Genet. 16: 151-162 (1990), discloses inhibition of galactosyltransferase-associated (GTA) protein expression by transcription of an RNA which is homologous to AU-rich elements (AREs) in the 3' untranslated region of the gta gene, which are believed to be important regulatory sequences.

Although gene suppression is quite useful for scientific studies of gene function and holds considerable promise for certain applications in disease therapy and genetic modification of plants and animals, current methods for identifying effective genetic suppressor elements (GSEs) are time consuming and arduous. Interference by dominant negative mutant proteins, for example, either requires extensive knowledge about the functional domain structure of the protein so that reasonably promising candidate mutant proteins can be prepared, or necessitates individual preparation and screening of numerous candidate mutant proteins. Antisense RNA and competitive homologous RNA similarly require extensive individual preparation and screening of candidate inhibitory sequences, absent considerable knowledge about important specific sequences within the RNA. There is, therefore, a need for generalized methods for identifying and isolating GSEs which will allow simplified determination of effective elements without undue experimentation or extensive structure/function knowledge. An ideal method would allow simultaneous analysis of multiple possible candidate GSEs, regardless of their mechanism of action.

BRIEF SUMMARY OF THE INVENTION

The invention relates to the suppression of specific gene function in eukaryotic or prokaryotic cells. More particularly, the invention relates to nucleotide sequences which are capable of suppressing gene function when expressed in a living cell. These nucleotide sequences are known as genetic suppressor elements. Existing methods of suppressing gene function in living cells require considerable information about the structure and function of the gene products, i.e., specific RNA sequences or specific protein domains. Alternatively, existing methods of suppressing gene function can be applied in the absence of detailed structure/function information, but at the expense of the considerable time and effort required to produce many individual mutant proteins or many complementary or homologous RNA or DNA sequences. In contrast, the invention provides a general method for obtaining effective genetic suppressor elements (GSEs) for cloned genes or viruses, without extensive structure/function information, and in a simple selection or screening procedure.

The invention is made possible by two discoveries. First, the inventors have discovered that small peptide fragments, corresponding to only a minute portion of a protein, can inhibit the function of that protein in vivo, even without mutation of the fragments. Second, the inventors have demonstrated that certain random small fragments of DNA, derived from a particular gene or virus, are capable of inhibiting that particular gene or virus in vivo, when they are expressed in a living cell, and that these fragments can be isolated by functional selection for suppression of the gene or virus.

In the method of the invention for obtaining GSEs, randomly fragmented DNA, corresponding to DNA sequences from a gene or virus to be inactivated, is transferred into an expression library capable of expressing the random fragments of DNA in a living cell. Desired living cells are then genetically modified by introducing into them the GSE expression library by standard procedures, and cells containing GSEs are isolated or enriched for by selecting or screening for gene suppression. GSEs are then obtained from the living cells exhibiting the gene suppression phenotype.

GSEs obtained by the method of the invention may be used to genetically modify cells by introducing the GSE into the cell such that it can be expressed and suppress gene function in the genetically modified cell. Alternatively, for some cell types it will be possible to obtain genetically modified cells bearing a gene suppression phenotype as a result of introduction of the GSE library, without ever having to first isolate the GSE.

Genetically modified cells according to the invention can provide benefits, such as virus resistance, which can be commercially important in biotechnology processes using living cells, as well as in food crops derived from virus-resistant cells, or even in agriculturally important transgenic animals. In addition, improved agricultural plants and animals can be produced from genetic modification by suppression of genes responsible for undesirable properties, e.g., cross-pollination of inbred plants. Finally, genetic modification according to the invention may be useful for human therapeutic applications, such as antiviral therapy.

DETAILED DESCRIPTION OF THE SPECIFIC EMBODIMENTS

Suppressing the function of specific genes by modifying cells to express gene-specific inhibitory substances is an important approach to various goals in biotechnology and medicine. One of these goals is inhibition of replication of pathogenic viruses in genetically modified cells.

Other suppression targets include, for example, genes associated with tumorigenicity (oncogenes) as well as genes responsible for some undesired properties of agricultural plants or animals. Specific suppression of a target gene requires expression of specially constructed genetic elements that generally include modified DNA sequences derived from the target gene. In one of the currently used approaches to gene suppression, all or a portion of cDNA of the target gene is inserted in a reverse orientation into an expression vector carrying a strong transcription promoter, so that antisense RNA is transcribed. Such antisense RNA can inhibit the function of the target mRNA molecules. Certain genes may also be functionally suppressed by expression of RNA sequences homologous to regulatory sequences in the mRNA. In another, more recent approach, mRNA sequences in an antisense orientation are combined with specific enzymatically active RNA sequences called ribozymes, which are capable of cleaving a target mRNA molecule. Another way to suppress gene expression is to use a mutant form of the target protein that can act in a dominant negative fashion by interfering with the function of the wild-type (normal) form of the same protein.

Although approaches to suppressing genes are thus known in the art, there are no general principles which provide guidance about how to derive DNA elements which can efficiently suppress gene function (genetic suppressor elements, or GSEs) without extensive structure/function information about the RNA or protein, or without undue experimentation. The present invention provides a general method for obtaining GSEs. The method of the invention requires only the availability of a cloned gene or DNA from a pathogenic virus or intracellularly parasitic microorganism targeted for suppression and the knowledge of a selectable phenotype associated with inactivation of the target gene. This method does not depend on any knowledge of the structure/- function organization of the protein encoded by the target gene or the genetic structure of the target virus or microorganism.

In a first aspect, the invention provides a convenient, general method for obtaining GSEs. In this method, purified DNA corresponding to the gene or genome to be suppressed is first randomly fragmented by enzymatic, chemical, or physical procedures. In a preferred embodiment, random fragments of DNA are produced by treating the DNA with a nuclease, such as DNase I. The random DNA fragments are incorporated as inserts in a gene suppression element library, using an expression vector which is capable of expressing the inserted fragments in the cell type in which gene suppression is desired. For general principles of DNase I partial digestion and library construction see *Molecular Cloning, A Laboratory Manual*, Sambrook et al., Eds., Cold Spring Harbor Laboratory, Cold Spring Harbor, N.Y. (1989). In certain embodiments the inserted fragment may be expressed as part of a fusion protein. In other embodiments the inserted fragment alone may be expressed. In another embodiment, ribozyme-encoding sequences may be inserted directly adjacent to the insert to allow for selection of most efficient ribozyme-antisense clones. In still other embodiments the gene suppression element library may be further modified by random mutagenesis procedures known in the art. The inserted fragments may be expressed from either a constitutive or an inducible promoter.

The GSE library is next used to genetically modify living cells of the type in which gene suppression is desired, by introducing the library into the cells by procedures well known in the art, e.g., bacterial or yeast transformation, or transfection of plant or mammalian cells. See, e.g., Keown et al., Methods Enzymol. 185: 527–536 (1990). The genetically modified cells containing effective GSEs can be screened for or selected in a variety of ways. For example, when the suppression is directed against a cytolytic virus, cells containing effective GSEs may be selected on the basis of cell survival upon virus infection and development of cytopathic effect. In another embodiment, suppression is directed against a non-cytolytic virus or against a gene encoding a cell surface antigen. In this embodiment, selection is against the presence of the viral or cell surface antigens. This is accomplished by reacting the genetically modified cells with specific primary antibodies against the viral or cell surface antigens. "Unsuppressed" cells may then be eliminated by the addition of complement, or may be separated from "suppressed" cells by addition of fluorescent secondary antibody against the primary antibody, followed by fluorescence-activated cell sorting. For a general description of immunological selection and screening techniques see Davis et al., *Microbiology*, Harper and Row, Philadelphia, Pa. (1980). In another embodiment, suppression is directed against genes that must be expressed in order for cells to grow under specific procedures. In this embodiment, cells containing effective GSEs can be selected by "suicide selection" procedures that select for cells which cannot grow in the selective medium. See Patterson et al., Methods Enzymol. 151: 121 (1982).

In yet another embodiment, suppression is directed against growth-suppressing genes, such as tumor suppressors. In this embodiment, cells containing effective GSEs may be screened on the basis of morphological transformation of cell colonies.

The GSE is finally obtained from the selected cells by procedures known in the art. In one embodiment, the GSE is isolated by use of the polymerase chain reaction with DNA obtained from the selected cells and with primers homologous to sites on the vector flanking the insert. In another embodiment, the GSE expression library may be prepared in shuttle vectors, allowing efficient recovery of shuttle vectors containing GSEs (See, e.g., Groger et al., Gene 81: 285–294 (1989); Rio et al., Science 227: 23–28 (1985) for examples of shuttle vectors). Of course, in bacteria simple plasmid isolation procedures can be employed directly on the bacterial clone expressing the genetically suppressed phenotype. Finally, GSEs can be isolated by standard cloning techniques well known in the art using vector specific probes although this might be more laborious than other embodiments herein described.

In a second aspect, the invention provides GSEs which are most likely more effective than existing GSEs, since GSEs obtained according to the method of the invention may be selected from a very large number of possible DNA sequences, whereas existing GSEs have been the result of trial and error analysis of only a few designs. GSEs obtained according to the methods of the invention may operate according to principles different from those behind existing gene suppression methods, since it is the gene suppression phenotype, and not the mechanism, which is selected. GSEs obtained according to the methods of the invention are useful for the genetic modification of living cells for scientific studies, for biotechnology processes, for agricultural purposes and for human and animal therapeutic purposes. In addition, oligonucleotide GSEs can be readily prepared which correspond to the nucleotide sequence of the GSE obtained according to the method of the invention. These oligonucleotides, which may be standard oligonucleotides, standard oligodeoxynucleotides or chemically modified derivatives of oligonucleotides or oligodeoxynucleotides, will be capable of inhibiting specific gene function, by virtue of homology to the identified GSE. Such oligonucleotide inhibitors will be particularly useful for pharmaceutical purposes.

In a third aspect, the invention provides genetically modified living cells that contain effective GSEs, whereby in such cells particular genes are suppressed by the expression of the GSEs. In a preferred embodiment, such genetically modified cells are produced by introducing into the cell, by standard procedures, an expression vector containing a specific GSE obtained by the method of the invention and capable of expressing the GSE in the cell. In another embodiment the genetically modified cell is obtained directly from selection of cells into which the GSE library has been introduced, without any previous isolation of the GSE contained in the genetically modified cell.

The following examples are provided as means for illustration and are not limiting in nature.

EXAMPLE 1

Suppression of Gene Function by Expression of a DNA Sequence Encoding a Small Polypeptide P-glycoprotein, the product of the human mdr1 gene, is a multidrug transporter that renders mammalian cells resistant to various lipophilic drugs by pumping these drugs out of cells. See Chen et al., Cell 47:381 (1986). A short segment of mdr1 cDNA, corresponding to exon 7 of the mdr1 gene and encoding a 57 amino-acid long peptide, was inserted by standard procedures into an expression vector (pneoMLV), containing a G418-resistance gene, neo, as a selectable marker. One of the constructs (construct 1) was made in such a way that the mdr1-derived sequence was preceded by the translation initiation codon at the 5'end. At the 3' end, this sequence was adjoined to an open reading frame present in the vector sequence, so that the mdr1-derived sequence formed the N-terminal portion of the resulting fusion peptide. In another construct (construct 2), the mdr1-derived sequence was preceded by the initiation codon and followed by a stop codon, giving rise to an entirely mdr1-derived 58 amino acid protein (including the initiating methionine). Constructs 1 and 2, as well as a control pSV2neo plasmid, were transfected into human KB-8-5 cells, which display a moderate amount of multidrug resistance due to mdr1 expression. Transfectants were selected with G418, and possible changes in P-glycoprotein function were tested by determining the levels of resistance of individual transfectants to the cytotoxic drugs vinblastine and colchicine.

All ten of the control transfectants obtained with pSV2neo had the same levels of drug resistance as the recipient KB-8-5 cell line. In contrast, twelve of fifteen transfectants obtained with construct 1 had significantly decreased levels of drug resistance (in some cases less than one-half the resistance of KB-8-5). Five of eight transfectants obtained with construct 2 also showed a significant decrease in drug resistance relative to control KB-8-5 cells. These results indicate that a short segment of P-glycoprotein, comprising only 4.5% of the protein length, can serve as a genetic suppressor element for P-glycoprotein function. There is no specific function presently associated with this segment of P-glycoprotein, although this segment includes the amino acid residue 185 known to be a determinant of the specificity of P-glycoprotein-drug interactions.

These results demonstrate that short protein fragments without a known function can serve as dominant negative inhibitors of the wild-type protein, suggesting that dominant negative inhibitors may be selected from a library expressing random short fragments of the target protein.

EXAMPLE 2

Preparation of an Antiviral Genetic Suppressor Element Library

Lambda phage DNA was fragmented by partial digestion with DNaseI in the presence of $Mn^{++}$ ions and NcoI linkers were added to the termini of the resulting fragments by blunt-end ligation after filling in the termini with T4 DNA polymerase and Klenow fragment of DNA polymerase I. Fragments of 350–450 bp size were then isolated after NcoI digestion and agarose gel electrophoresis. The fragment mixture was inserted into a plasmid expression vector pKK233-2, which carries a gene for ampicillin resistance and expresses inserted sequences using an IPTG-inducible trc promoter and a specific translation initiation region. See Amann et al., Gene 40: 183 (1985). The vector was modified to provide for appropriate termination of translation of the inserted segment by insertion of the DNA sequence 5' CATGGTGACTGACTGAAGCT 3' into the NcoI and HindIII sites of the polylinker. The ligated mixture was used to transform *E. coli* strain PLK-F' (sensitive to lambda), and a library of approximately 80,000 ampicillin-resistant clones was obtained.

EXAMPLE 3

Identification and Isolation of Genetic Suppressor Elements

To identify and isolate genetic suppressor elements in a library prepared as described in Example 2, the amplified library was tested for the presence of clones resistant to infection by bacteriophage lambda. A library comprising cells transformed with an insert-free pKK233-2 vector was used as a control. After IPTG induction, aliquots of $10^6$ cells from the amplified library and the control were infected with lambda phage and plated on ampicillin-containing plates. The multiplicity of infection was selected so as to allow for the survival of 1%–3% of the infected control bacteria. After the first infection, there was no major difference in the number of surviving cells between the library and the control cells. Plasmid DNA was then extracted from the mixture of approximately $3\times10^4$ library-derived colonies that survived phage infection, and this DNA was used to transform plasmid-free bacteria. The new library was also infected with lambda, and this time approximately 10% of the cells in the library were found to be resistant under the conditions of infection that allowed either 3% or 0.02% of the control cells to survive. Plasmids were then isolated from 30 surviving colonies and used individually to transform fresh *E. coli* cells. After infection with lambda, cells transformed with 28 of 30 selected plasmids showed resistance to lysis.

Parallel studies with the control plasmid showed no increase in the number of resistant colonies after three rounds of selection, indicating that the immunizing clones were specific to the lambda fragment library. Restriction enzyme analysis showed that almost all the plasmids carried NcoI inserts of the expecter size (350–450 bp). Based on the observed frequency of the resistant cells, approximately 0.3% of the clones in the original fragment library carried GSEs. Only a minority of the suppressing and infected bacterial colonies showed chromosomal integration of lambda sequences after infection, thus indicating that induction of lysogeny is not a major mechanism for protection by the suppressing clones.

Another library was prepared as described in Example 2, except that the insert fragments were of an average size of 600–700 bp. Although this library also contained suppressing clones, their frequency was an order of magnitude lower than in the 350–450 bp library.

These results demonstrate that random fragmentation of DNA homologous to a gene whose function is to be suppressed, followed by library construction and biological selection or screening, is a feasible general approach for the isolation of genetic suppressor elements.

EXAMPLE 4

Characterization of Genetic Suppressor Elements

Eleven clones isolated according to Example 3 which carry fragments of lambda phage DNA and are capable of rendering *E. coli* immune to lambda-mediated lysis, have been characterized by partial DNA sequencing. Three of the clones were found to carry fragments of late genes of lambda (A, FI and R), inserted in inverse orientation relative to the promoter, indicating that these clones expressed antisense RNA for the corresponding genes. The other eight clones contained inserts expected to express sense-strand RNA for the corresponding genes. One of these clones contained the entire gene cro, which encodes a regulatory protein known to suppress the expression of the early genes of lambda. Expression of cro in the transformed cells would therefore be expected to prevent the phage replication. Surprisingly, the remaining seven clones contained DNA fragments corresponding to lambda genes believed to be inessential for either lytic growth or lysogeny. One of these clones contains the 5' half of a gene termed Ea31, that codes for an endonuclease whose role is unknown. The deletion of one half of the protein in our clone suggests that it may represent a dominant negative mutant of Ea31. The other six clones correspond to the gene Ea8.5, which encodes a 93 amino acid protein without a known function. Two of the six clones may contain the entire Ea8.5 gene, and the other four clones encode a truncated Ea8.5 protein, which is missing 8 to 30 amino acids at the C-terminus or 6 amino acids at the N-terminus. When plated on maltose-containing McConkey medium, bacteria expressing Ea8.5 sequences are deficient in maltose uptake. This indicates that lambda resistance provided by these clones is probably due to the inhibition of phage adsorption onto the cell surface, since a maltose transport protein, LamB, is known to serve as the lambda phage receptor. Suppression of the lambda receptor may be a normal function of the Ea8.5 gene, or wild-type Ea8.5 might have a different regulatory effect on the receptor, the observed suppression being the consequence of the suppressor clones being dominant negative mutants.

The present results indicate that the random fragment selection strategy can select for efficient genetic suppressor elements acting by at least three different mechanisms: utilization of the naturally evolved suppressor proteins (cro and Ea8.5), antisense RNA, and apparently also interference of dominant negative mutants at the protein level. Regulation of the lambda receptor expression by a lambda gene (Ea8.5) appears to be an entirely novel observation, in spite of an enormous body of work on the biology of lytic infection by phage lambda. This finding of a previously unknown regulatory mechanism in the life cycle of lambda and identification of a function for an "accessory gene", see Hendrix, et al., Eds. Lambda II. Cold Spring Harbor Laboratory, Cold Spring Harbor, N.Y. (1983), of this phage demonstrates the potential of the random fragment selection strategy of the invention for generating important functional information and identifying previously unsuspected means for gene suppression.

EXAMPLE 5

Derivation of Anti-HIV-1 Genetic Suppressor Elements

Cloned human immunodeficiency virus-1 (HIV-1) cDNA is digested with DNase I, filled-in, fitted with linkers and size-selected, as described in Example 2. The fragment mixture is transferred into a retroviral expression vector that carries a dominant selectable marker and is capable of infecting human T cells. The HIV fragment/retroviral vector library is used to infect a human T cell line that is susceptible to killing by HIV-1 and infected cells are selected for the presence of the dominant marker. The mixture of selected cells is exposed to HIV-1, and cytopathic effect is allowed to develop to completion. Surviving cells are expanded and their DNA is isolated. DNA sequences corresponding to HIV-1 fragments are obtained by amplification of isolated cellular DNA using the polymerase chain reaction (PCR) with primers specific for the retroviral vector on either side of the insert.

PCR-generated DNA fragments are fitted with linkers and transferred to the same retroviral vector that was used to prepare the first library to create a secondary library. The same T cell line that was used for the initial library is then infected with the secondary library. Infected cells are selected for the presence of the dominant marker and individual selected clones are tested for resistance to killing by HIV-1. Resistant clones, containing putative anti-HIV-1 GSEs are used for the isolation of the putative GSE by the polymerase chain reaction, as described above. The candidate GSEs are then individually inserted into the same retroviral vector and tested for the ability to protect T-cells against cytopathic effects of HIV-1.

EXAMPLE 6

Derivation of Anti-Tobacco Mosaic Virus (TMV) Genetic Suppressor Elements

Total TMV cDNA is randomly fragmented as described in Example 2. The fragment mixture is then transferred into an expression vector containing a neomycin phosphotransferase II gene such that the inverted fragment is transcribed, initiating from the cauliflower mosaic virus 35S promoter and terminating in the polyadenylation signal from the nopaline synthase gene. Leaf disks of tobacco are inoculated with *Agrobacterium tumefaciens* cells containing the expression library. Transformed cells are selected in culture for kanamycin resistance. Kanamycin resistant cells are then exposed in culture to TMV and cytopathic effect is allowed to develop. DNA is collected from transformed TMV-resistant cells and the insert fragments are amplified by the polymerase chain reaction, using primers homologous to the DNA sequences adjacent to the insert site. Amplified sequences are transferred into the same expression vector as used to make the initial library and again used to transform *A. tumefaciens*. Tobacco leaf disks are once again inoculated with the library in *A. tumefaciens* and kanamycin-resistant cells are again tested for TMV resistance. Individual TMV-resistant clones are used for the isolation of GSEs by the polymerase chain reaction, as described above. Candidate GSEs are then used to prepare individual GSE expression vectors, which are inserted in *A. tumefaciens* to inoculate tobacco leaf disks. Inoculated leaf disks are selected for kanamycin resistant cells, from which self-pollinated individual seedlings are produced and tested for TMV resistance.

We claim:
1. A method of obtaining genetic suppressor elements comprising the steps of:
   (a) randomly fragmenting DNA homologous to the gene to be suppressed, to yield DNA fragments of about 700 base pair or less;
   (b) transferring the DNA fragments to expression vectors to yield a library, wherein the expression vectors are capable of expressing the DNA fragments in a living cell in which gene suppression can be selected or screened;
   (c) genetically modifying living cells by introducing the genetic suppressor element library into the living cells;

(d) isolating or enriching for genetically modified living cells containing genetic suppressor elements by selecting or screening for gene suppression, and;

(e) obtaining the genetic suppressor element from the genetically modified cells.

2. A method of obtaining living cells containing genetic suppressor elements comprising the steps of:

(a) genetically modifying the living cells by introducing a library comprising randomly fragmented DNA sequences of about 700 base pairs or less; wherein the DNA sequences are homologous to a portion of the gene to be suppressed, and wherein the library is capable of expressing the DNA sequences in the living cell, and;

(b) isolating or enriching for genetically modified living cells containing genetic suppressor elements by screening or selecting for gene suppression.

3. A genetically modified living cell, containing genetic suppressor elements of about 700 base pairs or less, obtained according to the method of claim 2.

* * * * *

UNITED STATES PATENT AND TRADEMARK OFFICE
CERTIFICATE OF CORRECTION

PATENT NO. : 5,217,889
DATED : June 8, 1993
INVENTOR(S) : Igor B. Roninson et al.

It is certified that error appears in the above-identified patent and that said Letters Patent is hereby corrected as shown below.:

At column 1, insert the following below the title and before the "Background of the Invention" heading:

- -This invention was made with Government support under grants CA 39365 and CA 40333 awarded by the National Institutes of Health. The Government has certain rights in the invention. - -

Signed and Sealed this

Seventh Day of October, 1997

BRUCE LEHMAN

*Attest:*

*Attesting Officer*   Commissioner of Patents and Trademarks

UNITED STATES PATENT AND TRADEMARK OFFICE
CERTIFICATE OF CORRECTION

PATENT NO.       : 5,217,889
APPLICATION NO.  : 07/599730
DATED            : June 8, 1993
INVENTOR(S)      : Roninson et al.

It is certified that error appears in the above-identified patent and that said Letters Patent is hereby corrected as shown below:

STATEMENT OF GOVERNMENT INTEREST
This invention was made with government support under grants CA-56736-02 by the National Institutes of Health. The government has certain rights in the invention.

Signed and Sealed this

Twenty-ninth Day of January, 2008

JON W. DUDAS
*Director of the United States Patent and Trademark Office*